(12) United States Patent
Highland

(10) Patent No.: US 7,909,602 B1
(45) Date of Patent: Mar. 22, 2011

(54) ORTHODONTIC CHAIN ELASTIC

(76) Inventor: Kenneth J. Highland, San Jose, CA (US)

( * ) Notice: Subject to any disclaimer, the term of this patent is extended or adjusted under 35 U.S.C. 154(b) by 317 days.

(21) Appl. No.: 11/811,097

(22) Filed: Jun. 8, 2007

(51) Int. Cl.
*A61C 3/00* (2006.01)

(52) U.S. Cl. .......................................................... 433/18

(58) Field of Classification Search .................... 433/11, 433/13, 15, 18; 132/251, 259, 260, 321, 132/329, 328; 24/300, 301
See application file for complete search history.

(56) References Cited

U.S. PATENT DOCUMENTS

| | | | | |
|---|---|---|---|---|
| 5,238,404 A | * | 8/1993 | Andreiko | 433/20 |
| 5,461,133 A | * | 10/1995 | Hammar et al. | 528/10 |
| 6,254,383 B1 | * | 7/2001 | White | 433/18 |
| 6,280,186 B1 | * | 8/2001 | Logan | 433/11 |
| 2006/0147869 A1 | * | 7/2006 | Hekimian | 433/13 |
| 2008/0153052 A1 | * | 6/2008 | Ianieri et al. | 433/11 |

* cited by examiner

*Primary Examiner* — Ralph A. Lewis
*Assistant Examiner* — Eric Rosen

(57) ABSTRACT

An orthodontic chain elastic is disclosed. The orthodontic chain elastic includes end portions, two intermediate portions disposed between the end portions and a middle portion disposed between the two intermediate portions. Pluralities of apertures are formed in each of the end portions, the intermediate portions, and the middle portion. The end portions have a greater cross section than that of the intermediate portions that in turn have a greater cross section than that of the middle portion.

19 Claims, 3 Drawing Sheets

ORTHODONTIC CHAIN ELASTIC

BACKGROUND OF THE INVENTION

1. Field of the Invention

The present invention generally relates to orthodontic appliances and more particularly to an orthodontic chain elastic having varying inter-aperture spacing and regions having differing cross sections resulting in varying force levels along the length thereof.

2. Description of Related Art

It is known to use chain elastic or power chain to close spaces between teeth in orthodontic applications. Conventional chain elastic is generally uniform in construction and sold in 15-foot lengths. Three formats are offered that are commonly called continuous, short and long formats which indicates the uniform distance between the holes in the chain. Each format has a uniform force based upon a uniform thickness and construction of the device. When stretched distances as presented from hole to hole in the chain are equivalent. The continuous format is used to apply high closing forces, the short format is used to apply medium closing forces, and the long format is used to apply weaker closing forces.

The teeth in the mouth vary in the amount of root surface that is embedded in the gingiva or gums. Because the root surface area varies, the amount of force needed to move the various teeth differs. In addition, the spacing between the brackets affixed to the various teeth is not uniform. The generally uniform construction and spacing of conventional chain elastic limits its use as it cannot be easily adapted to meet the needs of the orthodontist confronted with patients having teeth of varying root surface and varying inter-bracket distances. Also it is common that bracket sizes for lower and anterior teeth are smaller that bracket sizes for upper and posterior teeth.

The use of the chain elastic having a generally uniform construction is further limited in that the elastic material may fail if it is stretched beyond its elastic limit. Such a condition may occur in attempting to bridge a large inter-bracket distance.

There is a need in the art for an orthodontic chain elastic that overcomes these limitations of the prior art. The orthodontic chain elastic is preferably capable of applying varying amounts of force to teeth having different amounts of root surface. The orthodontic chain elastic is also preferably configured to accommodate varying inter-bracket distances.

SUMMARY OF THE INVENTION

The orthodontic chain elastic in accordance with the invention comprises a chain elastic having varying inter-aperture spacing and regions having differing cross sections along the length thereof to provide varying force levels. The apertures are generally rectangular and sized to fit over orthodontic brackets affixed to a patient's teeth. The apertures vary in size to accommodate varying sized brackets. The chain elastic may comprise an elastomeric material including rubber and plastics.

In accordance with one aspect of the invention, an orthodontic chain elastic includes end portions, two intermediate portions disposed between the end portions and a middle portion disposed between the two intermediate portions. Pluralities of apertures are formed in each of the end portions, the intermediate portions, and the middle portion. The end portions that coordinate with the posterior of the mouth have a greater cross section to create greater force levels to the teeth than that of the intermediate portions that in turn have a greater cross section to create greater force levels than that of the middle portion that will coordinate with the anterior of the mouth.

In accordance with another aspect of the invention, an orthodontic chain elastic includes a plurality of apertures formed in rectangular portions, ones of a plurality of sections of round cross section connecting the plurality of rectangular portions one to the other, and wherein the ones of the plurality of sections of round cross section have differing cross sections.

In accordance with yet another aspect of the invention, an orthodontic chain elastic for use in providing closing forces to teeth having affixed thereto brackets, the orthodontic chain elastic including end portions, two intermediate portions disposed between the end portions and a middle portion disposed between the two intermediate portions, the end portions, the two intermediate portions and the middle portion comprising a non-hydroscopic elastomeric material, a plurality of apertures formed in the end portions, a plurality of apertures formed in the intermediate portions, and a plurality of apertures formed in the middle portion, the pluralities of apertures sized and configured to receive the base portions of the brackets, and wherein the end portions have a higher modulus of elasticity than that of the two intermediate portions which in turn have a higher modulus of elasticity than that of the middle portion to thereby provide varying closing forces appropriate for teeth having varying root surfaces.

There has been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended herein.

In this respect, before explaining at least one embodiment of the invention in detail, it is to be understood that the invention is not limited in its application to the details of functional components and to the arrangements of these components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

These and other aspects and features of the present invention will become apparent to those ordinarily skilled in the art upon review of the following description of specific embodiments of the invention in conjunction with the accompanying figures, wherein.

DETAILED DESCRIPTION OF A PREFERRED EMBODIMENT OF THE INVENTION

The present invention will now be described in detail with reference to the drawings, which are provided as illustrative examples of the invention so as to enable those skilled in the art to practice the invention. Notably, the figures and examples below are not meant to limit the scope of the present invention. Where certain elements of the present invention can be partially or fully implemented using known components, only those portions of such known components that are necessary for an understanding of the present invention will be described, and detailed descriptions of other portions of such known components will be omitted so as not to obscure the invention. Further, the present invention encompasses present and future known equivalents to the components referred to herein by way of illustration.

Figure 1:
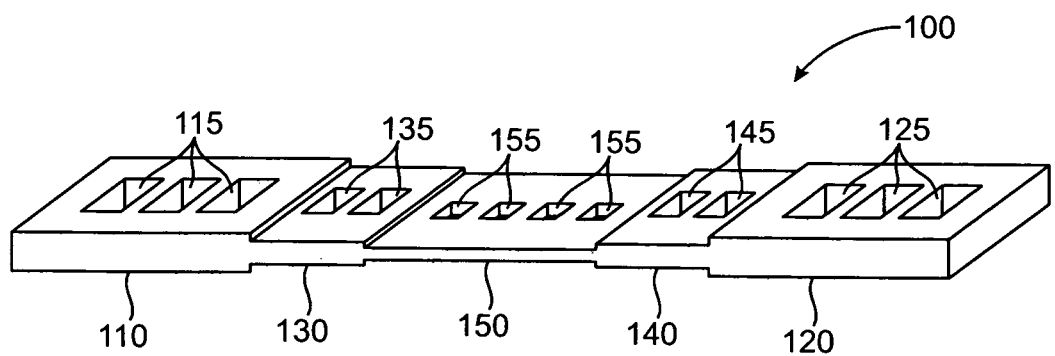
FIG. 1 is a perspective view of an orthodontic chain elastic in accordance with the invention.

A preferred embodiment of an orthodontic chain elastic generally designated 100 is shown in FIG. 1. The chain elastic 100 includes a length of non-hydroscopic elastomeric material such as rubber and plastic and generally has a rectangular cross section. The chain elastic 100 may be formed by cutting a tape of elastomeric material or by injection molding.

Portions 110 and 120 comprise end portions of the chain elastic 100 and have a relatively larger cross section than intermediate portions 130 and 140 and a middle portion 150 and thus will create a greater force with equivalent stretch. The higher cross section of the end portions 110 and 120 provide greater inter-bracket forces to brackets engaged by apertures 115 and 125 formed in the end portions 110 and 120 respectively when the chain elastic 100 is in use. These greater inter-bracket forces are particularly suited to move the patient's posterior or molar teeth.

Formed intermediate the end portions 110 and 120 are the intermediate portions 130 and 140 each having a relatively lower cross section than that of the end portions 110 and 120. The relatively lower cross section of the intermediate portions 130 and 140 provide relatively lower inter-bracket forces to brackets engaged by apertures 135 and 145 formed in the intermediate portions 130 and 140 respectively when the chain elastic 100 is in use. These relatively lower inter-bracket forces are particularly suited to move the patient's bicuspid teeth.

Middle portion 150 is formed intermediate the intermediate portions 130 and 140 and has a relatively lower cross section relative to that of the intermediate portions 130 and 140. The relatively lower cross section of the middle portion 150 provides relatively lower inter-bracket forces to brackets engaged to apertures 155 formed in the middle portion 150 when the chain elastic 100 is in use. This relatively lower inter-bracket force is particularly suited to move the patient's anterior or incisor teeth.

Apertures 115 and 125 formed in the end portions 110 and 120 are spaced apart such that when the chain elastic 100 is in use (i.e. stretched), the apertures 115 and 120 engage the brackets affixed to the patient's molar teeth. Apertures 135 and 145 formed in the intermediate portions 130 and 140 are spaced apart such that when the chain elastic 100 is in use, the apertures 135 and 145 engage the brackets affixed to the patient's bicuspid teeth. Apertures 155 formed in the middle portion 150 are spaced apart such that when the chain elastic 100 is in use, the apertures 155 engage the brackets affixed to the patient's incisor teeth. As the molar teeth are larger than the bicuspid teeth, which in turn are larger than the incisor teeth, the inter-bracket spacing of the apertures 115 and 125 is greater than the inter-bracket spacing of the apertures 135 and 145. The inter-bracket spacing of the apertures 155 is less than the inter-bracket spacing of the apertures 135 and 145.

Apertures 115 and 125 are preferably sized to receive brackets conventionally affixed to the molar teeth of the patient. These brackets are generally larger than the brackets affixed to the bicuspid teeth that in turn are generally larger than the brackets affixed to the incisor teeth. Correspondingly, the apertures 135 and 145 are smaller than the apertures 115 and 125 and larger than the apertures 155.

Figure 5:
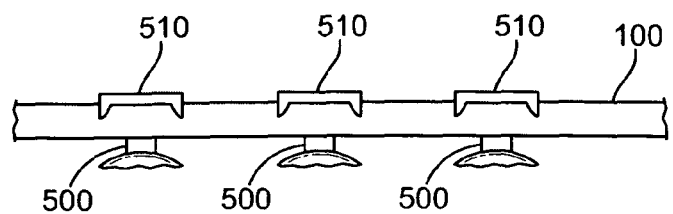
FIG. 5 is a partial top view of the orthodontic chain elastic of FIG. 1 in use in accordance with the invention.
Figure 6:
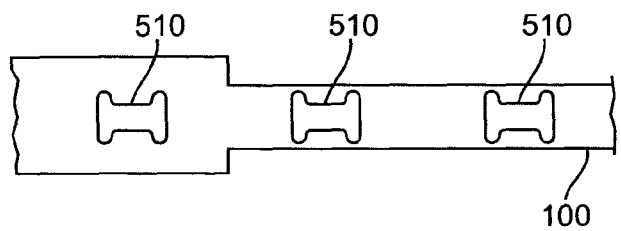
FIG. 6 is a partial front elevation view of the orthodontic chain elastic of FIG. 1 in use in accordance with the invention.

The apertures 115, 125, 135, 145 and 155 are preferably rectangular in configuration to seat around the rectangular bases 500 of brackets 510 as shown in FIGS. 5 and 6. The rectangular configuration advantageously provides for greater contact between the chain elastic 100 and the brackets 510 than chain elastics of the prior art.

Figure 3:
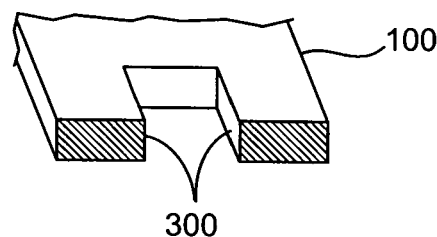
FIG. 3 is a cross sectional view of the orthodontic chain elastic of FIG. 1 in accordance with an aspect of the invention.
Figure 4:
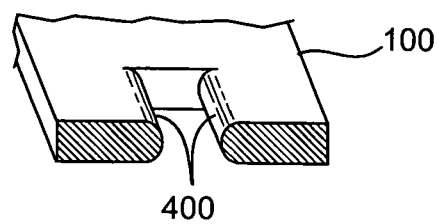
FIG. 4 is a cross sectional view of the orthodontic chain elastic of FIG. 1 in accordance with another aspect of the invention.

The configuration of the walls of the apertures may be flat or rounded. With reference to FIG. 3, walls 300 are flat. Rounded walls 400 are shown in FIG. 4. In use, rounded walls 400 are less susceptible to tearing.

Figure 2:
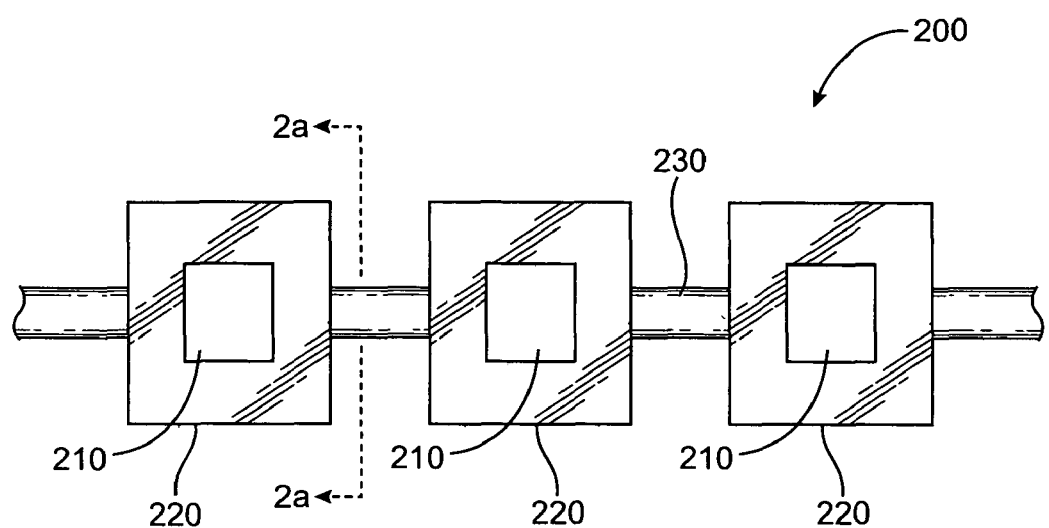
FIG. 2 is a partial top plan view of an alternative embodiment of the orthodontic chain elastic in accordance with the invention.

An alternative embodiment of the invention is partially shown in FIG. 2 and includes an orthodontic chain elastic generally designated 200. In contrast to the chain elastic 100 wherein the distances between the apertures 115, 125, 135, 145, and 155 are bridged by rectangular sections of the body of the chain elastic 100, these same distances are bridged by sections 230 of round cross section to provide for less surface area that can be attacked by fluids in the patient's mouth.

Chain elastic 200 includes a plurality of apertures 210 of rectangular configuration sized to receive brackets affixed to the patient's teeth. The apertures 210 are formed in generally rectangular portions 220 and have varying dimensions to conform to the size of the brackets used on particular teeth including molar, bicuspid and incisor teeth.

Figure 2A:
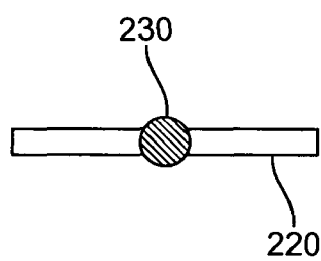
FIG. 2a is a cross sectional view of the orthodontic chain elastic of FIG. 2

Distances between apertures 210 also vary to generally conform to the distances between brackets when the chain elastic 200 is in use. Sections 230 of generally round cross-section as shown in FIG. 2a bridge the distances between portions 220. The chain elastic 200 also provides for varying forces along its length. This is achieved by varying the size of cross sections of the sections 230. In this embodiment, it is desirable that the working elastic limit exceed 300% stretch for sections 230 of the chain 200 that connect from bracket to bracket.

Figure 7:
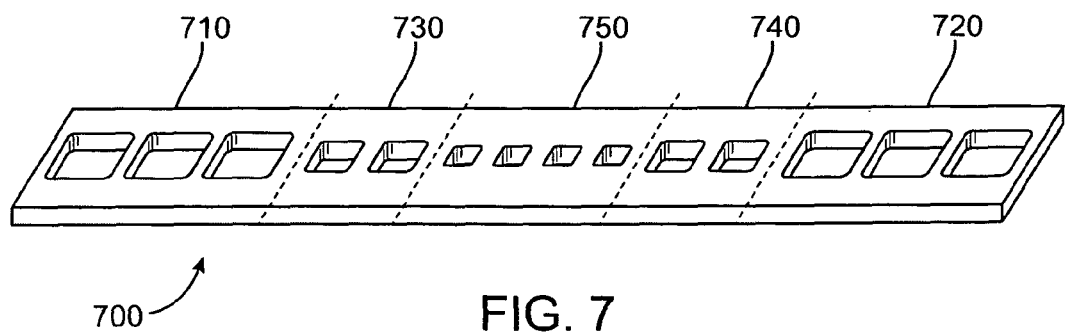
FIG. 7 is a perspective view of an alternative embodiment of an orthodontic chain elastic in accordance with the invention.

With reference to FIG. 7, an alternative embodiment of the invention includes an orthodontic chain elastic generally designated 700 having portions of identical cross section but of varying modulus of elasticity's. End portions 710 and 720 have a same modulus of elasticity that is relatively greater than the modulus of elasticity of intermediate portions 730 and 740 which in turn have a relatively greater modulus of elasticity than a middle portion 750. The portions of varying modulus of elasticity's provide for differing closing forces to teeth requiring differing closing forces. The orthodontic chain elastic 700 is in all other respects (size, spacing and configuration of apertures, and material composition) as the orthodontic chain elastic 100.

The orthodontic chain elastics 100, 200 and 700 have a length shorter than the arch to which it is applied and may be available in various lengths to accommodate various size mouths.

The orthodontic chain elastic of the invention provides a chain elastic that is easy to fit onto orthodontic brackets. The rectangular shape of the apertures of the chain elastic ensures that the apertures easily and snugly fit onto the rectangular bases of the brackets to exert maximum force to the brackets and to minimize tearing of the chain elastic. The portions of the chain elastic having differing cross sections or modulus of elasticity's provide for differing forces to teeth requiring differing closing forces. The varying inter-bracket spacing of the apertures along the chain elastic provide for apertures conforming to the varying inter-bracket spacing of the brackets affixed to the patient's teeth.

It is apparent that the above embodiments may be altered in many ways without departing from the scope of the invention. Further, various aspects of a particular embodiment may contain patentably subject matter without regard to other aspects of the same embodiment. Still further, various aspects of different embodiments can be combined together. Accordingly, the scope of the invention should be determined by the following claims and their legal equivalents.

What is claimed is:

1. An orthodontic chain elastic comprising:
   end portions, two intermediate portions disposed between the end portions and a middle portion disposed between the two intermediate portions;
   a plurality of apertures formed in the end portions, a plurality of apertures formed in the intermediate portions, and a plurality of apertures formed in the middle portion;
   wherein the plurality of apertures formed in the end portion, intermediate portions and middle portion are all aligned along a longitudinal axis of the orthodontic chain elastic; and
   wherein the end portions have a greater cross section than that of the two intermediate portions which in turn have a greater cross section than that of the middle portion;
   wherein the cross-sections are taken by planes extending perpendicular to the longitudinal axis.

2. The orthodontic chain elastic of claim 1, wherein the end portions, the two intermediate portions and the middle portion have a rectangular cross section.

3. The orthodontic chain elastic of claim 1, wherein the plurality of apertures formed in the end portions, the plurality of apertures formed in the two intermediate portions and the plurality of apertures formed in the middle portion are rectangular.

4. The orthodontic chain elastic of claim 3, wherein the plurality of apertures formed in the end portions, the plurality of apertures formed in the two intermediate portions and the plurality of apertures formed in the middle portion have flat walls.

5. The orthodontic chain elastic of claim 3, wherein the plurality of apertures formed in the end portions, the plurality of apertures formed in the two intermediate portions and the plurality of apertures formed in the middle portion have rounded walls.

6. The orthodontic chain elastic of claim 1, wherein the plurality of apertures formed in the end portions are of greater size than the plurality of apertures formed in the two intermediate portions which in turn are of greater size than the plurality of apertures formed in the middle portion.

7. The orthodontic chain elastic of claim 1, wherein the plurality of apertures formed in the end portions are spaced further apart than the plurality of apertures formed in the two intermediate portions which in turn are spaced further apart than the plurality of apertures formed in the middle portion.

8. The orthodontic chain elastic of claim 1, wherein the plurality of apertures formed in each end portion is three.

9. The orthodontic chain elastic of claim 1, wherein the plurality of apertures formed in each intermediate portion is two.

10. The orthodontic chain elastic of claim 1, wherein the plurality of apertures formed in the middle portion is four.

11. An orthodontic chain elastic comprising:
    a plurality of apertures formed in rectangular portions;
    a plurality of sections of round cross section connecting the plurality of rectangular portions one to the other; and
    wherein the ones of the plurality of sections of round cross section have differing cross sections.

12. The orthodontic chain elastic of claim 11, wherein the plurality of apertures are rectangular.

13. The orthodontic chain elastic of claim 12, wherein the plurality of apertures have flat walls.

14. The orthodontic chain elastic of claim 12, wherein the plurality of apertures have rounded walls.

15. The orthodontic chain elastic of claim 11, wherein the plurality of apertures have differing dimensions to accommodate brackets of differing dimensions.

16. The orthodontic chain elastic of claim 11, wherein the plurality of sections of round cross-section have differing lengths.

17. An orthodontic chain elastic for use in providing closing forces to teeth having affixed thereto brackets, the orthodontic chain elastic comprising:
    end portions, two intermediate portions disposed between the end portions and a middle portion disposed between the two intermediate portions, the end portions, the two intermediate portions and the middle portion comprising a non-hydroscopic elastomeric material;
    a plurality of apertures formed in the end portions, a plurality of apertures formed in the intermediate portions, and a plurality of apertures formed in the middle portion, the pluralities of apertures sized and configured to receive the base portions of the brackets; and
    wherein the end portions have a higher modulus of elasticity than that of the two intermediate portions which in turn have a higher modulus of elasticity than that of the middle portion to thereby provide varying closing forces appropriate for teeth having varying root surfaces.

18. The orthodontic chain elastic of claim 17, wherein the plurality of apertures formed in the end portions are of greater size than the plurality of apertures formed in the two intermediate portions which in turn are of greater size than the plurality of apertures formed in the middle portion.

19. The orthodontic chain elastic of claim 17, wherein the plurality of apertures formed in the end portions are spaced further apart than the plurality of apertures formed in the two intermediate portions which in turn are spaced further apart the plurality of apertures formed in the middle portion.

* * * * *